(12) United States Patent
Parida et al.

(10) Patent No.: US 8,423,339 B2
(45) Date of Patent: Apr. 16, 2013

(54) VISUAL ANALYSIS OF A PROTEIN FOLDING PROCESS

(75) Inventors: Laxmi P. Parida, Mohegan Lake, NY (US); Ruhong Zhou, Stormville, NY (US)

(73) Assignee: International Business Machines Corporation, Armonk, NY (US)

( * ) Notice: Subject to any disclaimer, the term of this patent is extended or adjusted under 35 U.S.C. 154(b) by 1443 days.

(21) Appl. No.: 11/627,128

(22) Filed: Jan. 25, 2007

(65) Prior Publication Data

US 2008/0183452 A1 Jul. 31, 2008

(51) Int. Cl.
*G06G 7/48* (2006.01)
*G06G 7/58* (2006.01)
*G01N 33/48* (2006.01)
*G01N 31/00* (2006.01)

(52) U.S. Cl.
USPC .............. 703/11; 703/12; 702/19; 702/22

(58) Field of Classification Search ............... None
See application file for complete search history.

(56) References Cited

U.S. PATENT DOCUMENTS 6,859,455 B1 * 2/2005 Yazdani et al. ............... 370/392
2008/0147360 A1 * 6/2008 Fejes et al. ........................ 703/2

OTHER PUBLICATIONS

Zhou et al. (Bioinformatics, 2007, 23(1), 99-106) available online Oct. 24, 2006.*
Cornell et al., (Journal of Molecular Graphics and Modeling, 2001, 19, 136-145).*
Feng et al., "Protein Folding Trajectory Analysis Using Patterned Clusters," Series on Advances in Bioinformatics and Computational Biology, as proceedings of Asia Pacific Bioinformatics Conference (APBC2005), Singapore, pp. 95-104, Jan. 17-21, 2005.
Parida, et al., "Combinatorial Pattern Discovery Approach for the Folding Trajectory Analysis of a β-Hairpin,"PLoS Computational Biology, Jun. 2005, vol. 1, Issue 1, pp. 32-40.
Zhou, et al., "The Free Energy Landscape for β Hairpin Folding in Explicit Water," PNAS, Dec. 18, 2001, vol. 98, No. 26, pp. 14931-14936.
Pitera, et al., "Understanding Folding and Design: Replica-Exchange Simulations of "Trp-cage" Miniproteins," PNAS, Jun. 24, 2003, vol. 100, No. 13, pp. 7587-7592.

* cited by examiner

*Primary Examiner* — Larry D Riggs, II
(74) *Attorney, Agent, or Firm* — Jose Gutman; Fleit Gibbons Gutman Bongini & Bianco PL

(57) ABSTRACT

A method, information processing system, and computer readable medium, are provided for analyzing a protein folding process. The method includes conducting an incremental pattern discovery process. The incremental pattern discovery process includes judging multidimensional data from a simulation of a protein folding process. The incremental pattern discovery process captures at least one intermediate data point in at least one pattern associated with the protein folding process.

13 Claims, 17 Drawing Sheets

$T_1$ is modified as the min. consensus of $T_1$ & $T_2$

MinConsensus($T_1$, $T_2$)
    $Nd_1$ = Root($T_1$), $Nd_2$ = Root($T_2$)
    If $Nd_i$, $i = 1; 2$, is a leaf node
        update location list of leaf node of $Nd_1$
        check if the location list (pattern) exists
    For each child $C_1$ of $Nd_1$
        Let child $C_2$ of $Nd_2$
            with Label($C_1$) = Label($C_2$)
            MinConsensus($C_1$, $C_2$)
    For each remaining child $C_2$ of $Nd_2$
        Introduce $C_2$ as a child of $Nd_1$
    Let $C^-$ be the child of $Nd1$ with label "-"
    For each child $C_j \neq C^-$ of $Nd_1$
        MinConsensus($C^-$, $C_j$)

FIG. 9

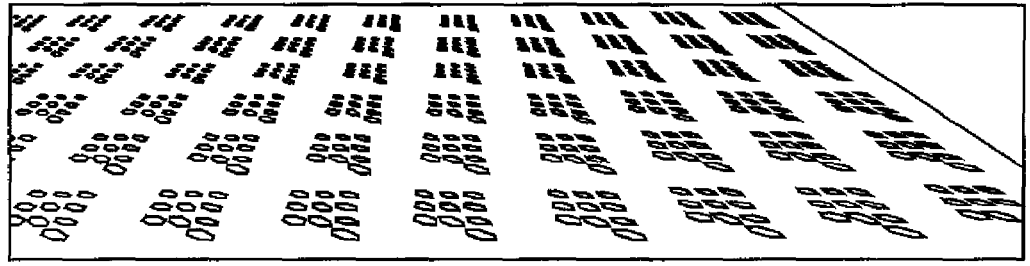
(a) t=0ns
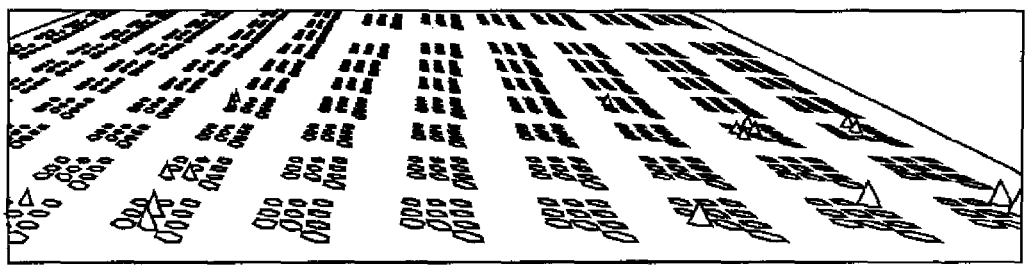
(b) t=1.25ns
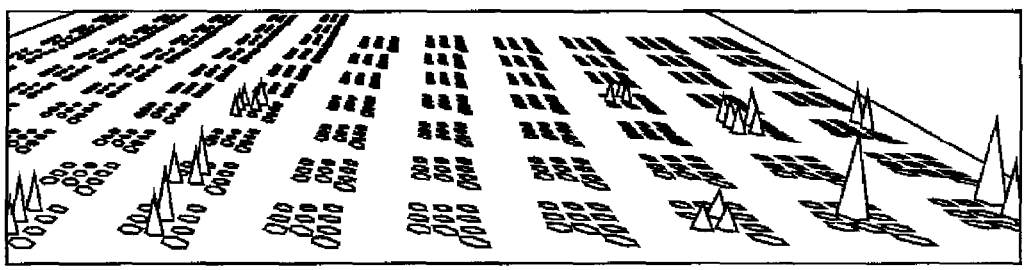
(c) t=2.5ns
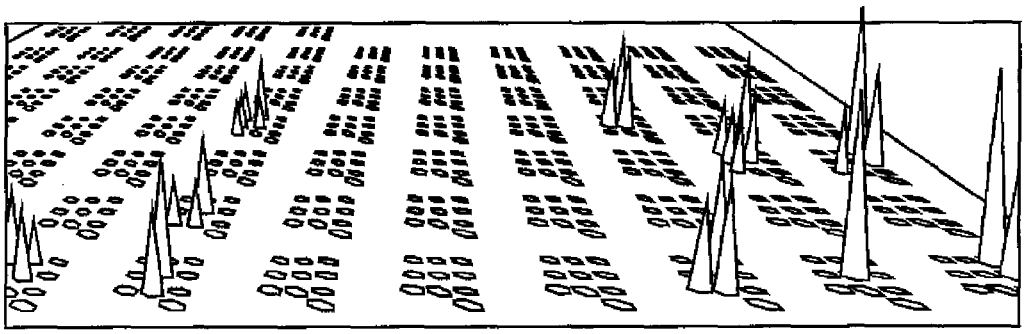
(d) t=5.0ns
FIG. 16 a b c

VISUAL ANALYSIS OF A PROTEIN FOLDING PROCESS

CROSS REFERENCE TO RELATED APPLICATION

This application is related to application "METHOD AND SYSTEM FOR PROTEIN FOLDING TRAJECTORY ANALYSIS USING PATTERNED CLUSTERS" Ser. No. 10/952,933, filed Sep. 30, 2004, now U.S. patent application Publication No. 2006/0069515, which is commonly assigned herewith to International Business Machines Corporation, and which is incorporated herein by reference in its entirety

FIELD OF THE INVENTION

The present invention generally relates to the field of computational biology and mechanisms behind protein folding, and more particularly relates to an incremental pattern discovery method (and system) for analyzing protein folding trajectory data from simulation experiments.

BACKGROUND OF THE INVENTION

Understanding how a protein folds into a functional or structural configuration is one of the most important and challenging problems in computational biology. The interest is not just in obtaining the final fold configuration (generally referred to as "structure prediction") but also understanding the folding mechanism and folding kinetics involved in the actual folding process. Many native proteins fold into unique globular structures on a very short time-scale. The so-called "fast folders" can fold into the functional structure from a random coil in microseconds to milliseconds.

Recent advances in experimental techniques that probe proteins at different stages during the folding process have shed light on the nature of the folding kinetics and thermodynamics. However, due to experimental limitations, detailed protein folding pathways remain unknown. Computer simulations performed at various levels of complexity, ranging from simple lattice models to all-atom models with explicit solvents, can be used to supplement experiments and fill in some of the gaps in knowledge about protein folding mechanisms.

Large scale simulations of protein folding with realistic all-atom models still remain a great challenge. Enormous effort is required to solve this problem. One example solution utilizes the recent IBM Blue Gene project, which is aimed at building a supercomputer with hundreds of teraflop to petaflop computing power to tackle the protein folding problem. However, effective analyses of the trajectory data from the protein folding simulations, either by molecular dynamics or MonteCarlo method, remains a great challenge due to the large number of degrees of freedom and the huge amount of trajectory data.

Currently, the protein folding mechanism is often characterized by calculating the free energy landscape versus reaction coordinates. Various reaction coordinates are used, such as the fraction of native contacts, the radius of gyration of the entire protein, the root mean square derivative (RMSD) from the native structure, the number of β-strand Hydrogen bonds, the number of α-helix turns, the hydrophobic core radius of gyration, and the principal components (PC) from principal component analysis (PCA). Principal component analysis (PCA) is a method of analyzing multivariate data in order to express their variation in a minimum number of principal components or linear combination of the original, partially correlated variables. Searching for improved reaction coordinates is still of great interest in protein folding mechanism studies.

FIG. 1 and FIG. 2 depict conventional free energy contour maps for analyzing protein folding trajectories. FIG. 1 is a free energy contour map illustrating the fraction of native contact ρ versus the radius of gyration of the entire peptide $R_g$ at 310K. FIG. 2 is a contour map illustrating the principal component PC-1 versus the principal component PC-2. This conventional method of plotting and analyzing contour maps is a manual method of analyzing protein folding trajectory data. As shown in FIG. 1 and FIG. 2, the conventional contour map analysis is limited in that it is two dimensional (e.g., only two reaction coordinates may be plotted and analyzed at a time). A problem with this conventional, manual method is that many protein folding configurations may be overlooked.

These analyses have provided important information for an improved understanding of protein folding. However, contour map analysis often requires a priori knowledge about the system under study and the free energy contour maps usually result in a large degree of information reduction due to their limit in dimensionality (e.g., which is limited to two or three). Thus, improved or complementary analysis tools are in great demand.

Additionally, conventional analyses methods are further limited in that they are generally manual processes. That is, "manual" in the sense that the data is plotted on contour maps, which are then visually analyzed. This manual operation increases the amount of time required to analyze the protein folding trajectory data. Furthermore, the manual operation limits the amount of protein folding trajectory data that may be analyzed, which limits the accuracy of the conventional analysis methods.

Therefore a need exists to overcome the problems with the prior art as discussed above.

SUMMARY OF THE INVENTION

Briefly, in accordance with the present invention, disclosed are a method, information processing system, and computer readable medium for analyzing a protein folding process. The method includes conducting an incremental pattern discovery process. The incremental pattern discovery process comprises judging multidimensional data from a simulation of a protein folding process. The incremental pattern discovery process captures at least one intermediate data point in at least one pattern associated with the protein folding process.

In another embodiment, an information processing system for analyzing a protein folding process is disclosed. The information processing system includes a memory and a processor that is communicatively coupled to the memory. An incremental pattern discovery module that is communicatively coupled to the memory and processor is also included in information processing system. The incremental pattern discovery module conducts an incremental pattern discovery process. The incremental pattern discovery process comprises judging multidimensional data from a simulation of a protein folding process. The incremental pattern discovery process captures at least one intermediate data point in at least one pattern associated with the protein folding process.

In yet another embodiment, a computer readable medium for analyzing a protein folding process is disclosed. The computer readable medium includes instructions for conducting an incremental pattern discovery process. The instructions for the incremental pattern discovery process further comprised instructions for judging multidimensional data from a simulation of a protein folding process. The incremental pattern discovery process captures at least one intermediate data point in at least one pattern associated with the protein folding process.

One advantage of the present invention is an integrated approach towards understanding the folding process via visual analysis of patterns of reaction coordinates is provided. Reaction coordinates can be produced with time and at each time interval, incremental patterns can be extracted from the reaction coordinates. Based on these incremental patterns an appropriate pattern landscape, which is animated over time can be displayed to a user. This integrated approach allows for a better understanding of a process such as that of the protein folding. Another advantage of the present invention is that a trie-based incremental pattern discovery algorithm is presented that allows for easy interpretation of and thus better understanding of the underlying protein folding process.

By using the presented visual analysis approach, crucial information about protein folding intermediates can be extracted. Structural motifs that were previously overlooked by the free energy landscape analysis can be identified. Force field artifacts can also be identified using the visualization approach of the present invention. In addition, time-correlated folding events or time-sequences of folding intermediates (e.g. which secondary structure forms earlier than the other, or vice versa) can be easily recorded with the visualization process on the fly.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 9 is pseudo code illustrating a minimal consensus tree algorithm according to an embodiment of the present invention;

FIG. 16 illustrates the animation of patterns in the Trp-cage folding versus time for one replica;

DETAILED DESCRIPTION

Figure 1:
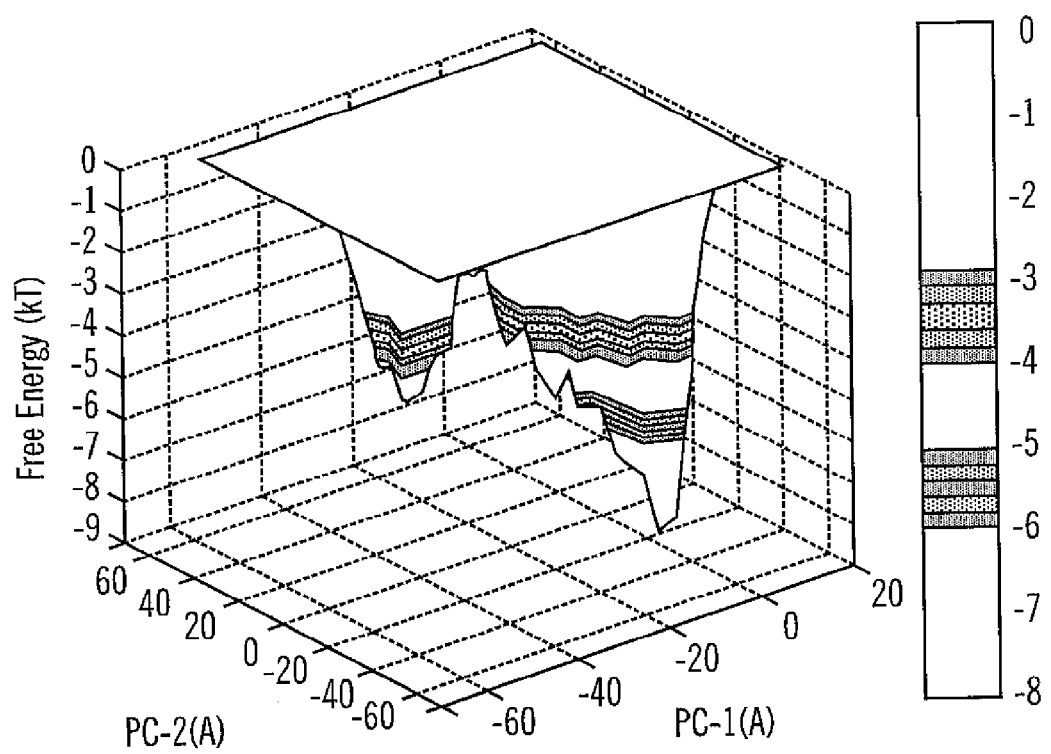
FIG. 1 is a free energy contour map of the fraction of native contact ρ and radius of gyration of the entire peptide $R_g$ at 310K.
Figure 2:
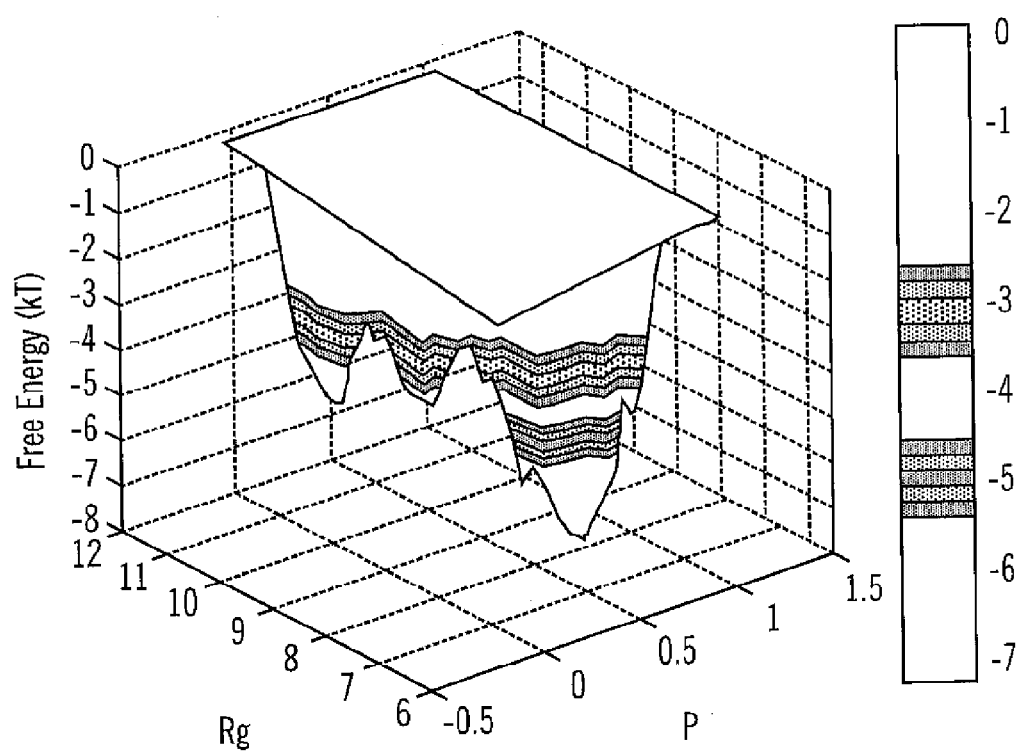
FIG. 2 illustrates a free energy contour map of the components PC-1 and PC-2.
Figure 3:
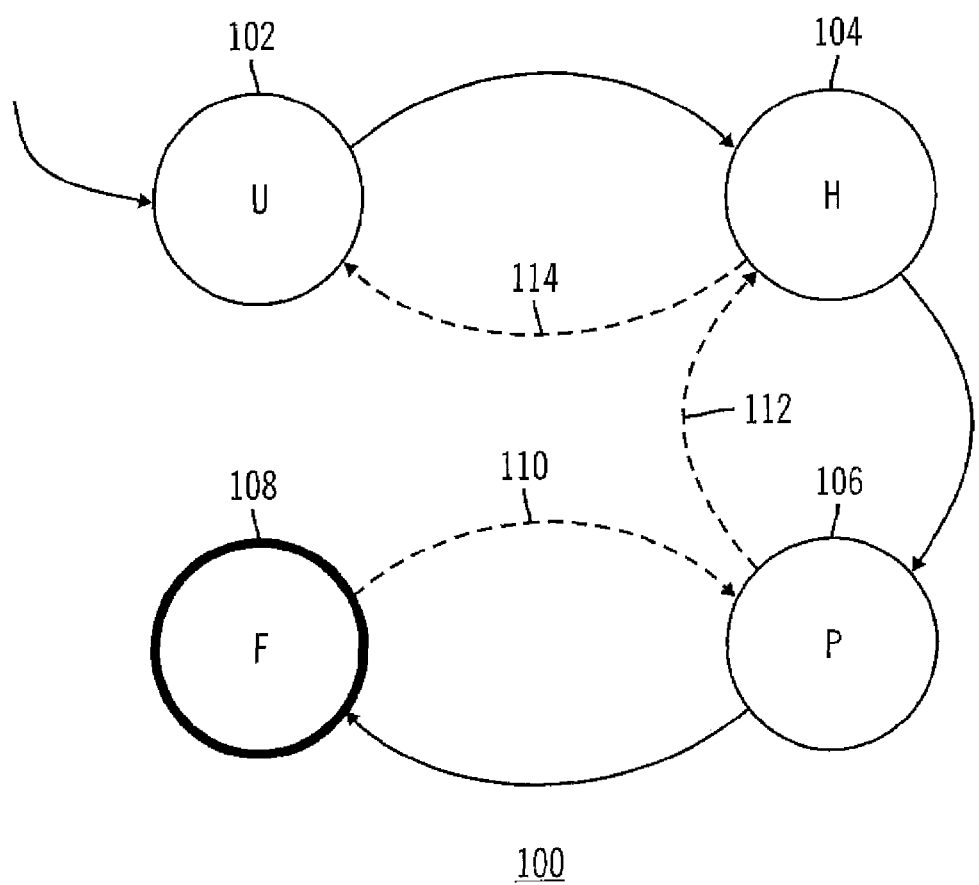
FIG. 3 is a schematic diagram illustrating a schema of a folding process of a hypothetical small protein.

The present invention as would be known to one of ordinary skill in the art could be produced in hardware or software, or in a combination of hardware and software. However in one embodiment the invention is implemented in software. The system, or method, according to the inventive principles as disclosed in connection with the preferred embodiment, may be produced in a single computer system having separate elements or means for performing the individual functions or steps described or claimed or one or more elements or means combining the performance of any of the functions or steps disclosed or claimed, or may be arranged in a distributed computer system, interconnected by any suitable means as would be known by one of ordinary skill in the art.

According to the inventive principles as disclosed in connection with the preferred embodiment, the invention and the inventive principles are not limited to any particular kind of computer system but may be used with any general purpose computer, as would be known to one of ordinary skill in the art, arranged to perform the functions described and the method steps described. The operations of such a computer, as described above, may be according to a computer program contained on a medium for use in the operation or control of the computer, as would be known to one of ordinary skill in the art. The computer medium, which may be used to hold or contain the computer program product, may be a fixture of the computer such as an embedded memory or may be on a transportable medium such as a disk, as would be known to one of ordinary skill in the art.

The invention is not limited to any particular computer program or logic or language, or instruction but may be practiced with any such suitable program, logic or language, or instructions as would be known to one of ordinary skill in the art. Without limiting the principles of the disclosed invention any such computing system can include, inter alia, at least a computer readable medium allowing a computer to read data, instructions, messages or message packets, and other computer readable information from the computer readable medium. The computer readable medium may include non-volatile memory, such as ROM, Flash memory, floppy disk, Disk drive memory, CD-ROM, and other permanent storage. Additionally, a computer readable medium may include, for example, volatile storage such as RAM, buffers, cache memory, and network circuits.

Furthermore, the computer readable medium may include computer readable information in a transitory state medium such as a network link and/or a network interface, including a wired network or a wireless network that allows a computer to read such computer readable information.

Protein Folding Process Schema

Well-known simulation methods exist to carry out the folding of a protein. However, it is often not sufficient to obtain a succinct understanding of the folding process. An exemplary and non-limiting aim of the present invention is to understand the folding mechanism via visual analysis of patterns of reaction coordinates. For example, the folding of a small protein (a chain of amino acids), β-hairpin, could be understood at a global level in terms of the states shown in FIG. 1. One advantage of the present invention is that it facilitates the understanding of the folding of every protein in this simplistic form. The conventional state-of-the-art analysis methods, however, are far from this goal.

Figure 4:
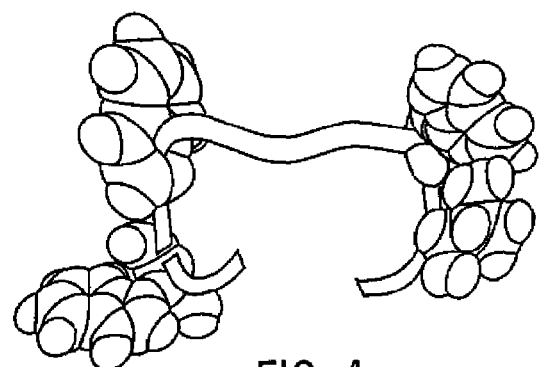
FIG. 4 is a schematic diagram illustrating a hypothetical protein in an unfolded state.
Figure 5:
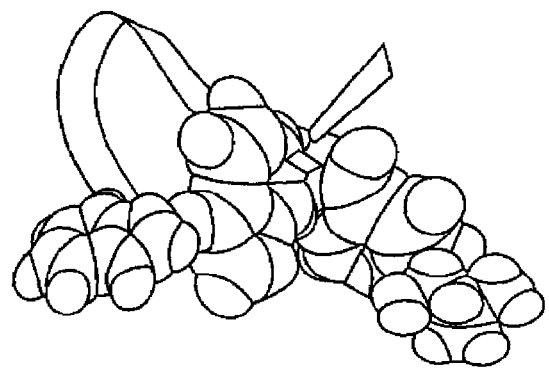
FIG. 5 is a schematic diagram illustrating a hypothetical protein in a hydrophobic core collapsed state.
Figure 6:
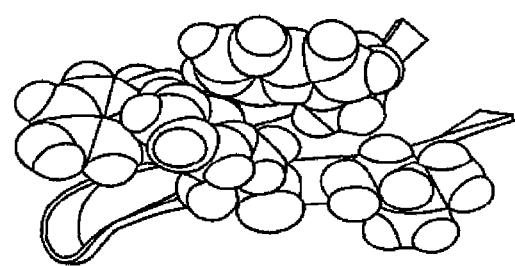
FIG. 6 is a schematic diagram illustrating a hypothetical protein in a partially folded state.
Figure 7:
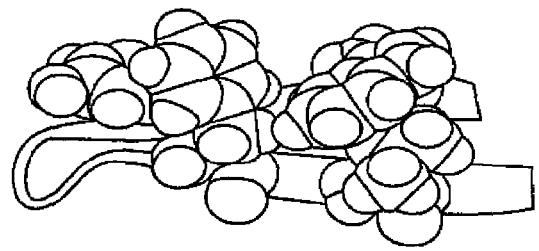
FIG. 7 is a schematic diagram illustrating a hypothetical protein in a folded state.

FIG. 1 illustrates a schema of the folding process 100 for a small protein. The exemplary protein illustrated in FIGS. 3-7 is the β-hairpin protein. It should be noted that the present invention is not limited to the β-hairpin. As shown in FIG. 1, the protein starts in an unfolded state (U) 102. FIG. 4 illustrates the β-hairpin protein in the unfolded state 102. The protein then changes to a hydrophobic core collapsed state (H) 104, as depicted in FIG. 5. The protein then moves to a partially folded (P) 106 state before finally ending at the folded state (F) 108. FIG. 6 depicts the β-hairpin protein in the partially folded state (P) 106 and FIG. 7 depicts the β-hairpin protein in the folded state (F) 108.

Each of the states (unfolded, hydrophobic core collapsed, partially folded, and folded) depicted in the folding process 100 are not necessarily stable. Therefore, once a protein moves to a partially folded state (P) 106, it may revert back to the unfolded state (U) 102 before finally reaching the folded state (F) 108, as depicted in FIG. 1 by the dashed, reverse arrows 110, 112, 114.

An embodiment of the present invention provides a three-step integrated process towards understanding the folding of a protein via visual analysis of patterns in reaction coordinates of the protein intermediates during the folding process. Thus, in one embodiment, as the protein folds, the changing landscape in the pattern space can be viewed via a patter visualization that illustrates an animated landscape. For example, a pattern visualization module can be used that updates the landscape with time. One advantage of the present invention is that it provides simultaneous multi-pronged views (e.g., folding protein and changing patterns landscape) of the process. The three-step process of the protein folding trajectory analysis method 800 of the present invention is depicted in FIG. 8.

In one embodiment, the three-step process is as follows 1.) protein folding simulation. 2.) pattern elicitation; and 3.) visualization of the patterns. In one embodiment, the protein folding process uses, but is not limited to, replica exchange molecular dynamics ("REMD"). REMD gives rise to a large collection of data points, each point being an array of the characteristic features of the folding protein at a specific time point. For example, such characteristic features may include the radius of gyration or the number of hydrogen bonds, etc. The REMD procedure couples molecular dynamics trajectories with a temperature exchange Monte Carlo process for efficient sampling of the conformational space. In this method, replicas are run in parallel at a sequence of temperatures ranging from the desired temperature to a high temperature at which the replica can easily surmount the energy barriers. From time to time, the configurations of neighboring replicas are exchanged. Because the high temperature replica can traverse high energy barriers, a mechanism is provided for the low temperature replicas to overcome the quasi ergodicity they would otherwise encounter in a single temperature replica. This method is essentially a Monte Carlo method. Thus, the time series is not strictly real time due to the random Monte Carlo exchange process. However, any suitable simulation procedure, either molecular dynamics (real time) or Monte Carlo (pseudo time), may be used.

Figure 8:
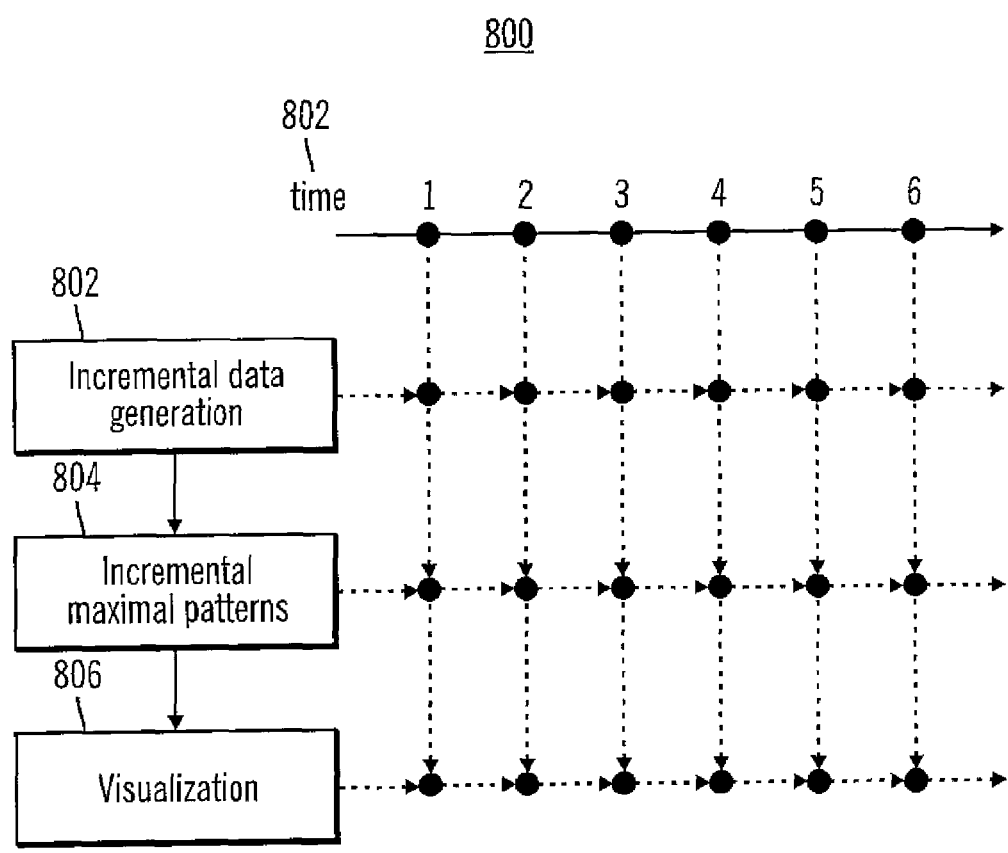
FIG. 8 is an operational flow diagram illustrating a process for visually analyzing protein folding according to an embodiment of the present invention.

FIG. 8 shows an incremental data generation process 802, which is the protein folding simulation process that produces the reaction coordinates data with time (e.g., the x-axis 803 in FIG. 8). At each time interval $t_\delta$, which in FIG. 1 $t_\delta=1$, the newly generated data is fed into an incremental maximal pattern generation module 804. The incremental maximal generational module 804, in one embodiment, extracts the patterns and feeds them to a visualization module 806. The visualization module 806, in one embodiment, displays an appropriate pattern landscape. The changing landscape, in one embodiment, is animated over time. One advantage of the present invention is that the integrated approach for understanding the folding process of a protein extracts crucial information about folding intermediates and identifies structural motifs that are previously overlooked by the free energy landscape analysis.

Incremental Pattern Discovery

The following illustrates the second process of pattern elicitation 804 using an incremental pattern discovery algorithm. Let D be an n×m array of real values where D[i,j] represents the value of property $J_j$ for the ith data point. A cluster pattern p, is a collection of $1 < l \leqq m$ columns $p = (J_{j_1} = c_{j_1}, J_{j_2} = c_{j_2}, K, J_{j_l} = c_{j_l})$ with quorum K, if there exist $K' \geqq K$ rows such that for each of these rows i, $(c_j - \delta_j) < D[i,j] < (c_j + \delta_j)$ holds for all $j_1 \leqq j \leqq j_l, \delta_j \geqq 0$ are specified for each column $J_j$. The collection of those K'rows is denoted by $L_p$.

A pattern p is maximal if there exists no pattern p', with $p' \supset p$ $\mathcal{L}'_p \subseteq \mathcal{L}_p$. In one embodiment, an on-line algorithm is used to discover cluster patterns as compared to using an off-line (i.e. given all the n rows of the input array D) algorithm. Each row i represents the data in time i. At time i, the rows 1, 2, . . . , i are available to the algorithm, i denoted as D[1K i,m]. Because maximal pattern p generated at time $t_1$ is displayed, it is important to assert that at time $t_2 > t_1$, p remains maximal. In one embodiment, the following assertion is made. A pattern p that is maximal in D[1K $t_1$,m] is also a maximal pattern in D[1K$t_2$,m], where $t_2 > t_1$. Since the data arrives one complete row at a time, a previously declared maximal pattern cannot become non-maximal later.

In one embodiment, a trie based algorithm is used for the incremental pattern discovery. For simplicity of exposition, assume that D is defined on $\Sigma = \{\sigma_1, \sigma_2, K\sigma_l\}$, with an ordering on the alphabet as $\sigma_1 < \sigma_2 < K < \sigma_l$. Let "-"$\in \Sigma$ and $\Sigma \cup \{$"-"$\}$ be denoted by $\Sigma^*$. Further, let $\sigma_i <$ "-" for all $1 \leqq i \leqq l$. In one embodiment, the incremental pattern discovery is based on a modified trie data structure cp-trie. As each row of D is read, it is treated as a string of length i and the cp-trie data structure is constructed having some special properties discussed below. A first property is that there is one root node whose depth is assumed to be 0. Each edge is labeled and the label of an internal node is assumed to be the label of the (unique) incoming edge. A second property is that the tree is of height m. An internal node at depth j from the root denotes the jth column of D.

A third property is an internal node that has more than one child also has a wild child, where the edge is labeled by "-". Each unique path from the root node to the leaf node A represents a pattern $p^A$ in D: if an edge at depth j is labeled with "-", then column j is ignored. Thus each leaf node A corresponds to a cluster pattern $p^A$ and has a pointer to $L_p^A$ or the set of rows that that have $p^A$. Therefore, a minimal consensus tree can now discussed.

Given trees $T_i$,i=1,K, k labeled on $\Sigma^*$,T is a consensus tree of the k trees, (1) if for each leaf node $A_i$ in $T_i$, there is a leaf node A in T with $p_{A_i}=p_A$ and, $\mathcal{L}_{pA_i}=\mathcal{L}_{pA}$ (2) for every leaf node A in T there is leaf node $A_i$ in $T_i$, for some i such that $p_A \subseteq p_{Ai}$, and (3) no two siblings of T have the same label (T is a trie). Further, T is a minimal consensus tree if it has no subtree T' that is a consensus of $T_i$,i=1,K,k.

A fourth property is that the sub-tree rooted at a node A with label "-" is the minimal consensus tree of sub trees $T_i$ that correspond to trees rooted at each sibling $A_i$ of A. This is well-defined due to the following result and the algorithm to compute the minimal consensus trees is outlined in FIG. 9. The minimal consensus tree T of labeled $T_i$,i=1,K,k is unique. The pattern discovery algorithm, in one embodiment, is based on constructing the cp-trie. Recall that at time i, the rows 1,2,K,i are available to the algorithm, denoted as D[1K i,m]. The following observation can be made. Let $T_i$ be the cp-trie corresponding to D[1K i,m]. Then $T_{i_1}$ is a subtree of $T_{i_2}$ for $i_1 < i_2$.

This shows that as each row is read, the cp-trie is augmented without any backtracking on the trie (tree) structure. However, the location lists pointed to by the leaf nodes may be augmented (but not reduced). This is also demonstrated in the example shown in FIG. 10. Next the algorithm is described through an example. Let $\Sigma=\{a<b<c<s<p<q<r<x<y<z\}$ and D have five columns $J_1$, $J_2$, $J_3$, $J_4$, $J_5$ defined as:

|   | $J_1$ | $J_2$ | $J_3$ | $J_4$ | $J_5$ |
|---|---|---|---|---|---|
| 1 | x | a | d | b | c |
| 2 | y | a | d | b | c |
| 3 | z | a | d | p | q |
| 4 | y | a | d | b | c |
| 5 | y | r | d | s | c |

Let T be the cp-trie under construction. When D is empty, T has only the root node. To add a new row i of D to T. This row is treated as a string of length m and added to the trie T in the standard way as is further described in (A. V. Aho, J. E. Hopcroft, and J. D. Ullman. *Data Structure and Algorithms*. Addison-Wesley Publishing Company, 1983.), which is incorporated by reference in its entirety. Further, this row is added to the location list pointed to by the leaf node. Let P be a node that has more than one child in T given as $A_i$,i=1,2,K,l. Using the MinConsensus( ) algorithm, a child with the label "-" is either created or updated. Recall that the labels are ordered. This ordering of the edge labels defines a unique left-to-right ordering of the leaf nodes. Let leaf nodes $p_1 < p_2$ in the left-to-right ordering of the cp-trie, (i.e leaf node $p_1$ is to the left of $p_2$) with $\pm_{p1}=\pm_{p2}$. Then $p_2$ must be non-maximal with respect to $p_1$.

Figure 10:
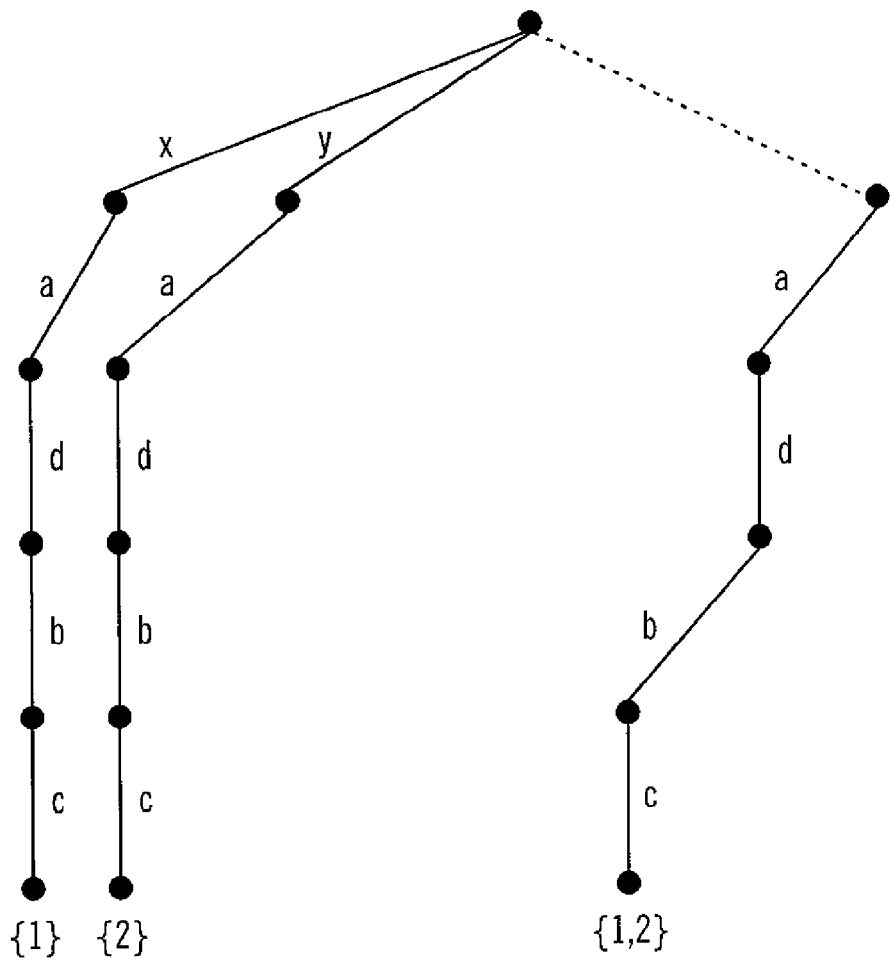
FIGS. 10-12 illustrates a stepwise construction of a cp-trie according to an embodiment of the present invention.
Figure 11:
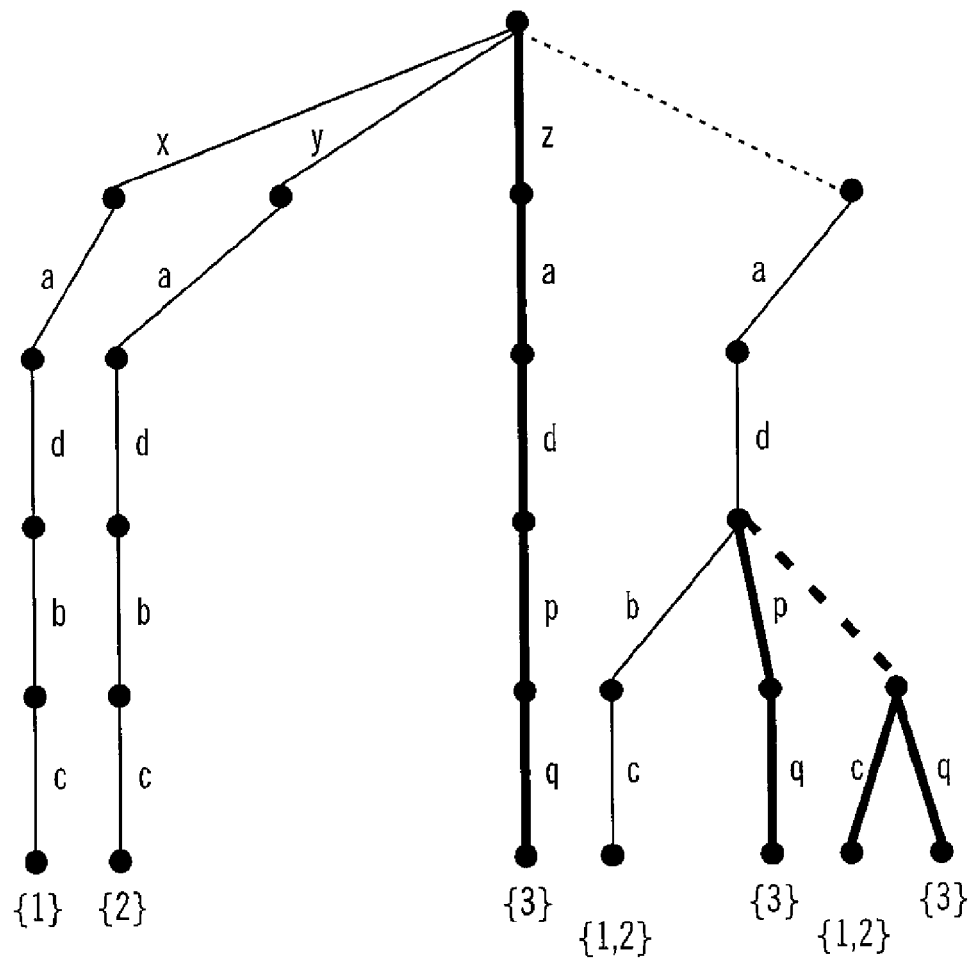
Figure 12:
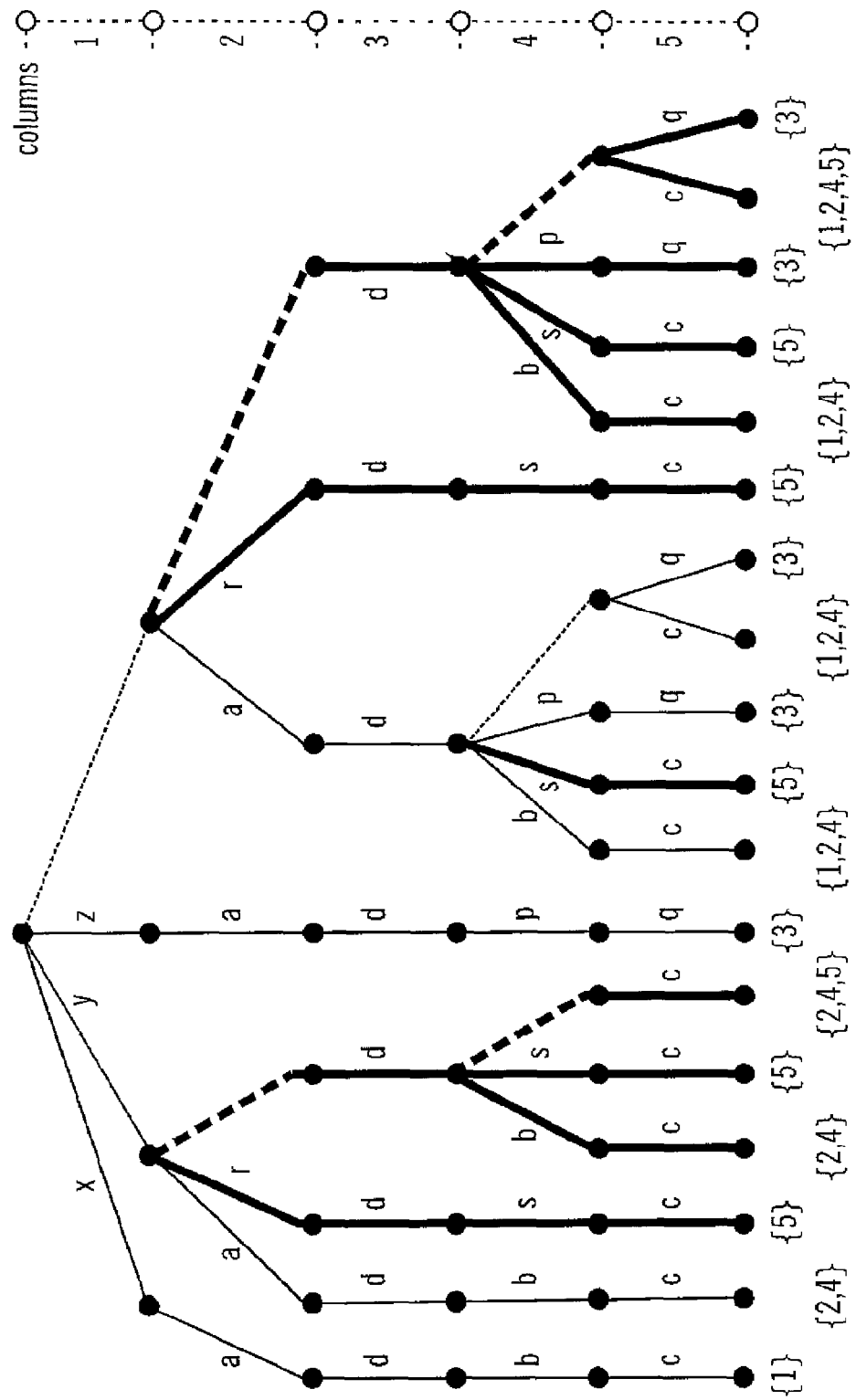

Since the wild edge is always the rightmost child, a pattern $p_1$ on the left is more specific than $p_2$ on the right, hence the above result holds. This property the pattern to be displayed as they are created (without ever having to backtrack). In the algorithm, as a new location list is generated, it is checked with existing location lists. The location lists are stored in a balanced binary tree to make this checking efficient. If it is a new list, the pattern is output as a maximal pattern. The stepwise construction of the cp-trie is shown in FIG. 10. The branches labeled with "-" are shown as dashed lines (the right most child of a node) for convenience. Here quorum is K=2. The maximal pattern $p_1$ is generated when row 2 is read; maximal pattern $p_2$ when row 4 is read; maximal patterns $p_3$ and $p_4$ when row 5 is read. The bold edges in FIG. 11 and FIG. 12 denote the new branches generated at that step.

Figure 13:
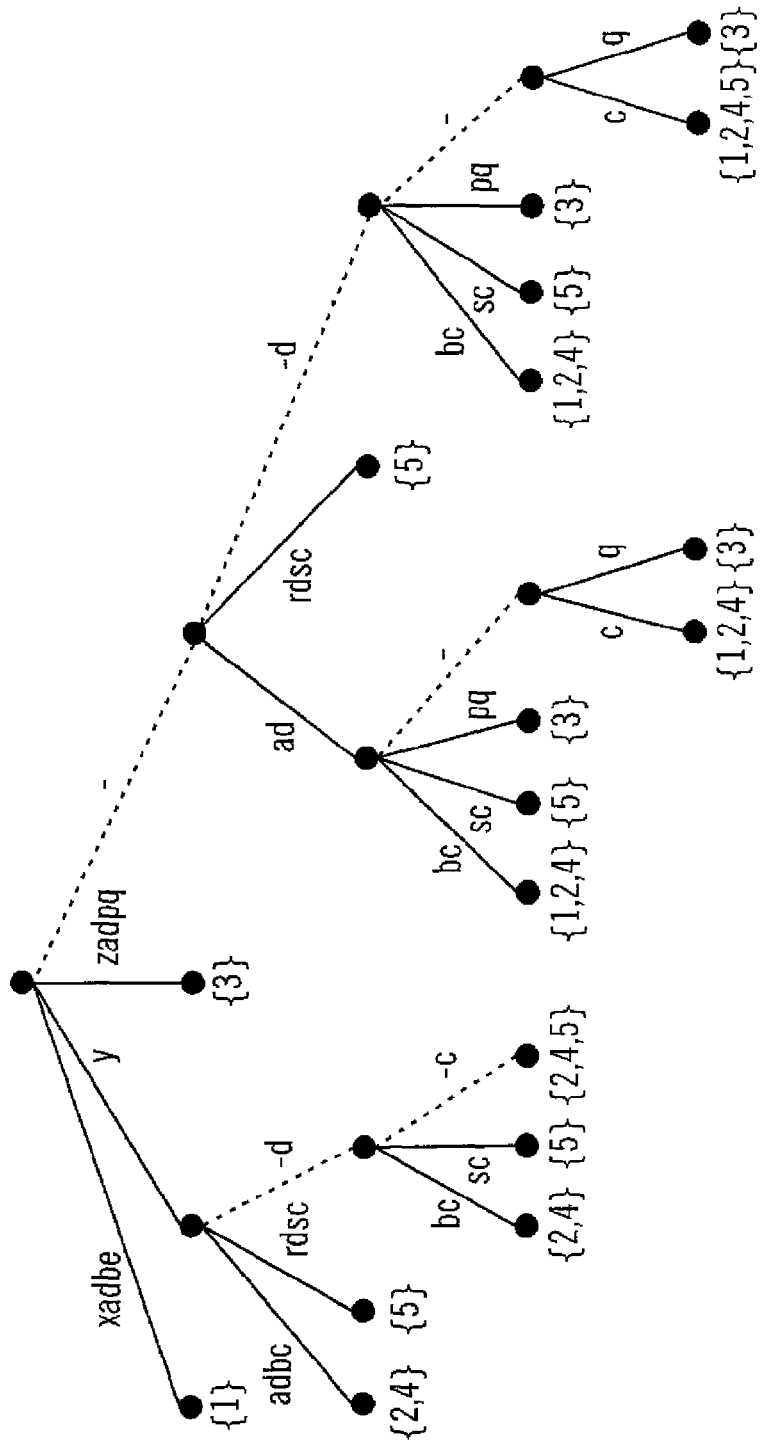
FIG. 13 illustrates a compact Patricia tree according to an embodiment of the present invention.

One advantage of the incremental pattern discovery process discussed above is that reaction coordinates can be produced with time and at each time interval, incremental patterns can be extracted from the reaction coordinates. Based on these incremental patterns an appropriate pattern landscape, which is animated over time can be displayed to a user. By using the presented visual analysis approach, crucial information about protein folding intermediates can be extracted. Structural motifs that were previously overlooked by the free energy landscape analysis can be identified. Force field artifacts can also be identified using the visualization approach of the present invention. In addition, time-correlated folding events or time-sequences of folding intermediates (e.g. which secondary structure forms earlier than the other, or vice versa) can be easily recorded with the visualization process on the fly. The current online (incremental) combinatorial approach takes the advantage of the observation that the pattern discovery problem at hand has a monotomic property that a pattern once is designated as maximal it stays as is. Another advantage of the online approach over the offline approach (previous work) is that a minimal amount of computation is required for the update, so it can be done in real time to facilitate the real-time animation Time Complexity In the application, D is defined on real values. The implications (worst case bounds and algorithm) of converting these real values to discrete characters is discussed (L. Parida and R. Zhou. Combinational pattern discovery approach for the folding trajectory analysis of a β-hairpin. *PLoS Computational Biology*, 1(1), 2005.), which is incorporated by reference in its entirety. In one embodiment, the same approach here in the on-line algorithm. Recall in the above application that m<<n. The cp-trie can be compacted to give a Patricia or a radix tree efficiency in space. FIG. 13 shows a compact Patricia tree for the running example.

In the worst case there can be $O(2^{md})$ distinct patterns where each column has at most d different values. Also, the location lists are stored in a balanced binary tree and the time to check if a list already exists takes $O(n \log n)$ time. At step i, let N be the number of patterns including the non-maximal patterns. Then the algorithm takes $O(Nn \log n)$ time at each step i.

Reducing the Pattern Space

It is quite clear that using maximality and quorum K is not adequate to control the number of patterns to be studied. In one embodiment, the following is one way of reducing this space without losing important information. Two patterns $p_1$ and $p_2$ are ∈-equal if $$\frac{|\mathcal{L}_{p1} \cap \mathcal{L}_{p2}|}{|\mathcal{L}_{p1} \cup \mathcal{L}_{p2}|} > \varepsilon$$

for some fixed $0 < \in \leq 1$. When two patterns $p_1$ and $p_2$ are ∈-equal, the two are replaced with $p=p_1 \cap p_2$, and $L_p=L_{p1} \cap L_{p2}$. Thus, in the reduced pattern space, no two distinct patterns $p_1$ and $p_2$ are ∈-equal.

Folding of a β-Hairpin

The above process of understanding the folding of a protein via visual analysis of patterns is first illustrated by example using a small but important protein system, the 16-residue β-hairpin protein from the C-terminus of protein G. An all-atom model is used for the description of the protein solvated in water. The Optimized Potential for Liquid Simulations—All-Atom (OPLS-AA) force field with an explicit solvent model, Simple Point Charge (SPC) model (both well-known), is used. A total of 64 replicas of the solvated system consisting of 4342 atoms are simulated with temperatures spanning from 270K to 695K. For each replica, a three nanosecond molecular dynamic simulation is run with replica exchanges attempted every 400 femtoseconds. For each conformation, seven different reaction coordinates are used as shown in Table 1. There are a total of about 20,000 conformations saved for each replica. Table 1 lists a small portion of the data for the replica at 310K (37 Celsius), which is the biological temperature.

TABLE 1

| $J_1$ $N_{HB}{}^\beta$ | $J_2$ $R_g{}^{core}$ | $J_3$ $R_g$ | $J_4$ $\rho$ | $J_5$ PC-1 | $J_6$ PC-2 | $J_7$ RMSD |
|---|---|---|---|---|---|---|
| 4.000 | 5.616 | 8.255 | 0.939 | −5.677 | −34.500 | 3.094 |
| 2.000 | 5.962 | 7.697 | 0.500 | 5.629 | −15.613 | 6.279 |
| 2.318 | 5.313 | 7.926 | 0.659 | −4.800 | −14.836 | 4.459 |
| 5.00 | 5.366 | 8.021 | 0.892 | −2.775 | −36.834 | 3.456 |
| 3.000 | 5.550 | 7.805 | 0.673 | −4.937 | −15.136 | 4.411 |
| 2.416 | 5.359 | 7.766 | 0.722 | −4.242 | −13.554 | 4.496 |
| 5.000 | 5.471 | 8.230 | 0.837 | −3.207 | −38.742 | 3.282 |
| 5.000 | 5.452 | 8.167 | 0.828 | −3.864 | −39.403 | 3.288 |
| 5.000 | 5.480 | 8.136 | 0.887 | −3.870 | −37.684 | 3.146 |
| 4.567 | 5.252 | 8.033 | 0.884 | −3.169 | −36.703 | 3.369 |
| 3.000 | 5.380 | 7.722 | 0.667 | −4.302 | −15.290 | 4.423 |
| 0.000 | 8.155 | 8.983 | 0.139 | −35.161 | 17.933 | 7.990 |

Table 1 provides raw data from the REM sampling of the β-hairpin folding in explicit water. Each column (i.e., $J_1$-$J_7$) corresponds to a different reaction coordinate/parameter. Each row of data points corresponds to data points taken at a specific time point. Table 1 depicts seven reaction coordinates. Specifically, column $J_1$ represents $N_{HB}{}^\beta$, the number of native β-strand hydrogen bonds. Column $J_2$ represents $R_g{}^{core}$, the radius of gyration of the hydrophobic core residues, tryptophan at position 43 (Trp43), tyrosine at position 45 (Tyr45), phenylalanine at position 52 (Phe52), and valine at position 54 (Val54). Column $J_3$ represents $R_g$ the radius of gyration of the entire protein.

Column $J_4$ represents ρ, the fraction of native contacts. Column $J_5$ represents PC-1, the first principal component from the Principal Component Analysis. Column $J_6$ represents PC-2, the second principal component. Column $J_7$ represents RMSD, the backbone root mean square deviation from the native structure. These seven reaction coordinates comprise the traditionally used parameters. However, any appropriate number or type of parameter may be used in place of these seven reaction coordinates. The parameters may be altered to determine the significant patterns extracted by the algorithm. These simulations have revealed the hydrophobic-core driven folding mechanism that is obtained from the free energy contour map analysis. Since this is a well studied system and a large amount of data is available, comparisons with other analysis tools, such as the free energy contour map analysis, might be easier and more straightforward. Various reaction coordinates obtained from previous experiments serve as the starting point for the present analysis.

Table 2 lists some representative patterns of size two with the above parameters.

| ID | Cluster Pattern | |
|---|---|---|
| 1 | $J_1 = 2.875 \pm 0.2$ | $J_2 = 5.448 \pm 0.6$ |
| 2 | $J_1 = 4.886 \pm 0.2$ | $J_2 = 5.448 \pm 0.6$ |
| 3 | $J_2 = 4.979 \pm 0.6$ | $J_4 = 0.819 \pm 0.15$ |

-continued

| ID | Cluster Pattern | |
|---|---|---|
| 4 | $J_2 = 5.871 \pm 0.6$ | $J_4 = 0.686 \pm 0.15$ |
| 5 | $J_3 = 7.840 \pm 0.6$ | $J_4 = 0.708 \pm 0.15$ |
| 6 | $J_3 = 7.840 \pm 0.6$ | $J_5 = -3.530 \pm 5.0$ |
| 7 | $J_4 = 0.819 \pm 0.15$ | $J_7 = 2.440 \pm 0.25$ |

Figure 14:
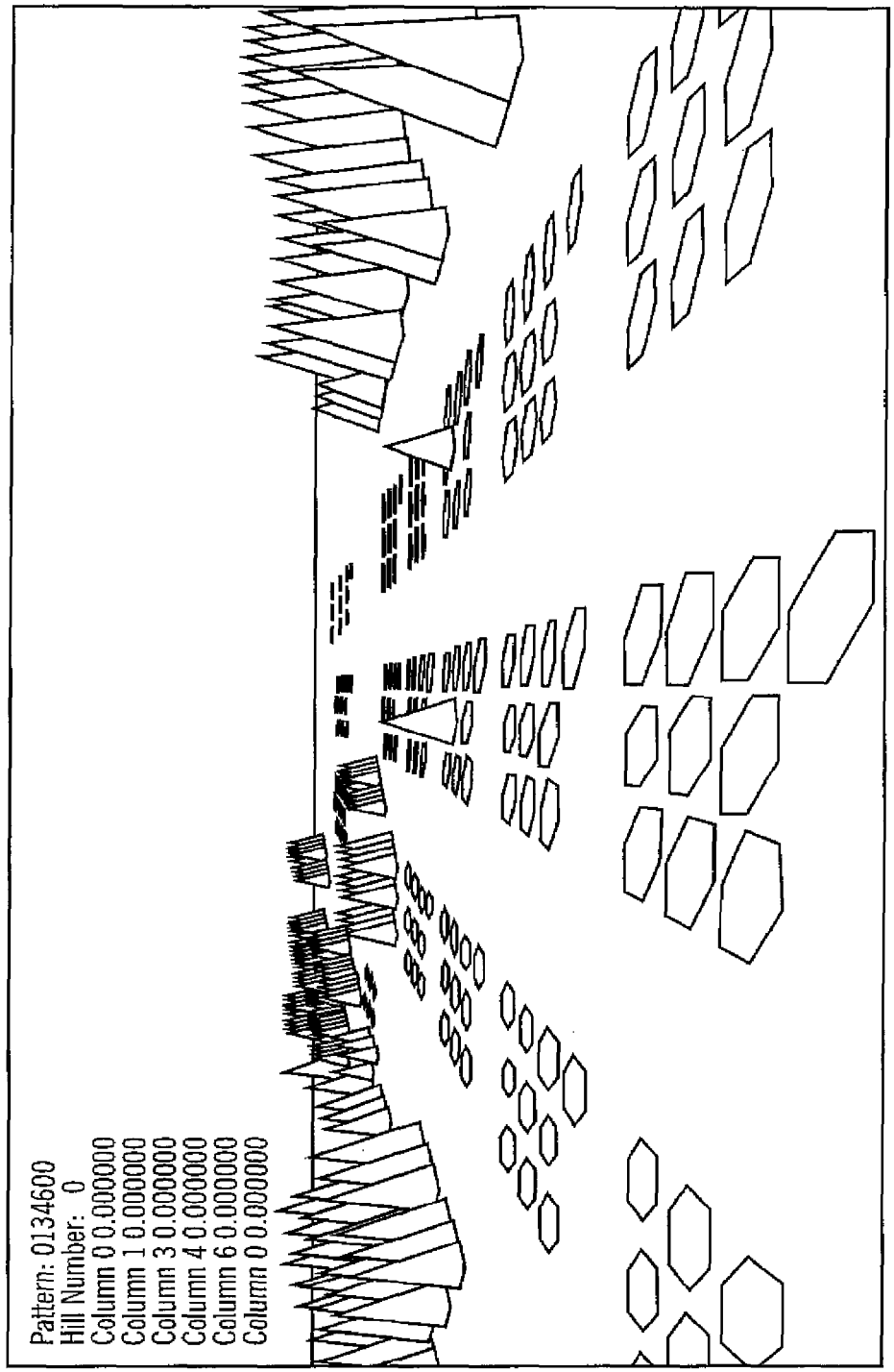
FIG. 14 illustrates the visualization of all patterns in a protein folding trajectory of a β-hairpin at 310K according to an embodiment of the present invention.

The term size in Table 2 refers to the number of reaction coordinates in the patterned cluster. FIG. 14 illustrates the time sequences of each of the patterns in Table 2. The time sequences of each pattern are used to animate the specific patterns with time. These simple patterns can be directly compared with the previous free energy states displayed in the free energy contour maps. Free energy contour maps are 3-D plots of free energy versus a pair of reaction coordinates or data columns of Table 2. While more complicated patterns such as those with up to six or seven reaction coordinates (shown as the spiked areas 1402 on the right hand side of FIG. 14) cannot be directly linked to the free energy contour maps due to the low dimensionality in these free energy landscapes, they can reveal more interesting results as discussed below.

Recovering Known Free Energy States

In one embodiment, the previously found free energy states can be recovered using a combinatorial pattern discovery approach as described in the published U.S. patent application Publication No. 2006/0069515 entitled "Method and System For Protein Folding Trajectory Analysis Using Patterned Clusters", which is hereby incorporated by reference in its entirety. FIG. 6 shows a representative or most populated structure for the first pattern in Table 2. This structure resembles the partially folded state, P state, in the free energy contour map analysis using reaction coordinates $N_{HB}{}^\beta$ and $R_g{}^{core}$. Similarly, the second pattern of Table 2 mimics very well the structure from the folded state (F state) in the same free energy landscape (see for example, FIG. 7). Thus this pattern resembles the F state of the free energy contour map. In general, there is a high degeneracy in patterns regarding to the (limited) folding states even with pattern reduction (unless a large ∈ is used in pattern reduction discussed above). For example, the 2nd, 3rd, and 7th patterns in Table 2 all represent the folded F state in the free energy landscape.

The method 800 of FIG. 8 discussed above improves the understanding of the protein folding mechanism by revealing important structures previously overlooked by conventional methods. A "hydrogen bond zipping" mechanism is conventionally known in which folding initiates at the turn and propagates toward the tails by making β-strand hydrogen bonds one-by-one, so that the hydrophobic core, from which most of the stabilization derives, form relatively late during the folding. It is known that the β-hairpin protein undergoes a hydrophobic core collapse first, then makes native β-strand hydrogen bonds one-by-one. In U.S. patent application Publication No. 2006/0069515, a different folding mechanism was proposed that this β-hairpin undergoes a hydrophobic core collapse first, then makes native β-strand hydrogen bonds to make over the free energy loss due to the loss of H-bonds between the backbone atoms and water.

Figure 15:
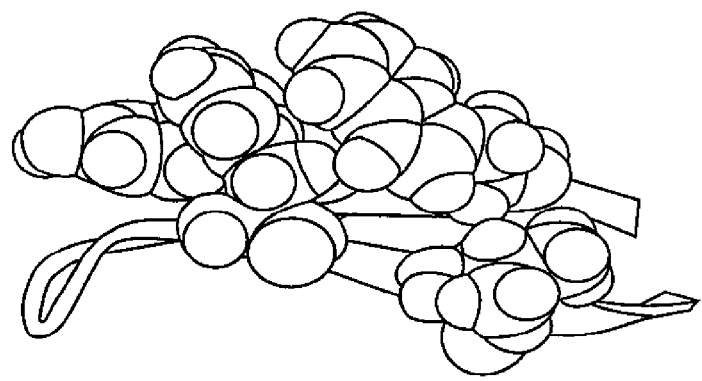
FIG. 15 is a schematic diagram illustrating a hypothetical protein where all of the five native β-strand H-bonds have been formed, but that the hydrophobic core is not completely aligned yet.

FIG. 15 shows a representative structure for the first pattern in Table 3, which lists patterns with multi-columns.

| ID | Cluster Pattern | | | | | |
|---|---|---|---|---|---|---|
| 1 | $J_1 = 4.950 \pm 0.2$ | $J_3 = 8.013 \pm 0.35$ | $J_4 = 0.848 \pm 0.15$ | $J_5 = -5.88 \pm 5.0$ | $J_6 = -33.6 \pm 16.5$ | $J_7 = 3.292 \pm 1.0$ |
| 2 | $J_2 = 5.748 \pm 0.6$ | $J_3 = 8.013 \pm 0.35$ | $J_4 = 0.848 \pm 0.15$ | $J_5 = -5.88 \pm 5.0$ | $J_6 = -33.6 \pm 16.5$ | $J_7 = 3.800 \pm 1.0$ |
| 3 | $J_1 = 4.903 \pm 0.2$ | $J_2 = 5.748 \pm 0.6$ | $J_3 = 8.013 \pm 0.35$ | $J_4 = 0.819 \pm 0.15$ | $J_5 = -3.86 \pm 5.0$ | $J_6 = -33.6 \pm 16.5$ $J_7 = 3.80 \pm 1.0$ |

The structure shows that all of the five native β-strand H-bonds have been formed, but that the hydrophobic core is not completely aligned yet. This represents a new class of intermediate configurations previously overlooked in conventional free energy landscape analysis.

The loop region also bends towards the hydrophobic core to somewhat offset the non-perfect hydrophobic core. These structures with H-bonds formed, but where the hydrophobic core is not perfectly aligned (RMSDs up to 4 Å). The loop region also bends towards the hydrophobic core to somewhat offset the non-prefect hydrophobic core. This implies that the β-hairpin can also have a path to form β-strand hydrogen bonds before the core is finalized. The current findings indicate that the final hydrophobic core and β-strand hydrogen bonds might be formed almost simultaneously. This can also be seen from the low free energy barrier in free energy landscapes.

Folding of the Trp-Cage

As discussed above, it is also important to study the time correlation between various folding patterns or states. For example, it is extremely useful to know which pattern or state precedes the other and by how much time. In one embodiment, this requires continuous trajectory data, ideally the true folding kinetics data. The following discussion uses another protein Trp-cage as an example to demonstrate this time-correlation feature. The current data was also obtained from the replica exchange molecular dynamics simulations, but the trajectory data were organized according to each replica which can climb up or down in temperature ladder (in the previous β-hairpin case discussed above, the trajectory was obtained at the fixed biological temperature 310K), thus these trajectories are continuous in the structural space. Even though the time sequences are not truly kinetic, they can still provide useful information on the time correlated or time dependent folding events.

The simulation details are briefly summarized in the following. An atomistic model is again used for the protein Trp-cage (304 atoms), but in a continuum solvent model to save CPU time. The AMBER force field (param 94, named AMBER94 thereafter) was used for simulation with the generalized Born/solvent accessible surface area (GB/SA) continuum solvent model. A dielectric constant of 78.5 is used for water and 1.0 for the protein in GB/SA, with a surface tension of 5.0 cal/mol/Å$^2$. A total of 12 replicas of the protein system was simulated at temperatures 273, 284, 298, 315, 333, 353, 375, 401, 431, 466, 506 and 555K. For each replica, a 5 ns molecular dynamics simulation is run (timestep 1 fs) with replica exchanges attempted every 5 ps and conformations saved every 0.5 ps. The reader is directed to for more details of the simulation. For each conformation frame, four slightly different reaction coordinates from the above β-hairpin case are calculated: (1) $R_g$: radius of gyration of the protein, (2) ρ: the fraction of native contacts, (3) RMSD: the $C_\alpha$ root mean square deviation (RMSD) from the native structure, (4) $N_{helix}$: the number of helical residues, including both the alpha-helices and $3_{10}$ helices. There are a total of 10,000 conformation frames saved for each replica.

Time Sequence of Folding Events

The time sequences of each pattern can be visualized through a visualization module. FIG. 16 shows a few snapshots of all the patterns at t=0 ns, 1.25 ns, 2.5 ns, and 5 ns for one replica from REMD. Some patterns, such as ($R_g$=7.914±0.5, $N_{helix}$=5.5±0.5), show up earlier than other patterns, indicating some structural patterns or intermediate structures develop in early stage of the folding. For example, this particular pattern, ($R_g$=7.914±0.5, $N_{helix}$=5.5±0.5), is found to be related to the alpha helix near residues 2-9 (see below). The time sequences when one particular pattern appears can be collected for each pattern, and consequently, collective patterns can be obtained at each time sequence window (window size 200-400 frames). For those time sequences with many patterns appearing at the same time, some structural signatures or motifs might be expected. Table 4 lists the top time sequences with most patterns identified in that time sequence window.

TABLE 4

The top time sequences with the most patterns collected from the pattern discovery approach.

| Sequence ID # | Start | End |
|---|---|---|
| 1 | 900 | 1100 |
| 2 | 1300 | 1500 |
| 3 | 2200 | 2400 |
| 3 | 2900 | 3100 |
| 4 | 3900 | 4100 |
| 5 | 4400 | 4600 |
| 6 | 5400 | 5700 |

As found previously, many patterns are redundant, for example, patterns ($R_g$=7.914±0.5, ρ=0.729±0.15), (ρ=0.729±0.15, RMSD=3.151±0.5, $N_{helix}$=8.5±0.5) and ($R_g$=7.914±0.5, ρ=0.729±0.15, RMSD=3.151±0.5, $N_{helix}$=7.5±0.5) all represent the folded state in this particular case.

Representative Structures in Folding Intermediates

It is of great interest to take a closer look at the structures in these time sequences since they might represent important intermediate folding events. The configuration frames corresponding to these time sequences can be fetched from the original trajectory file. The representative structures for each top time sequence window can be obtained by clustering.

Figure 17:
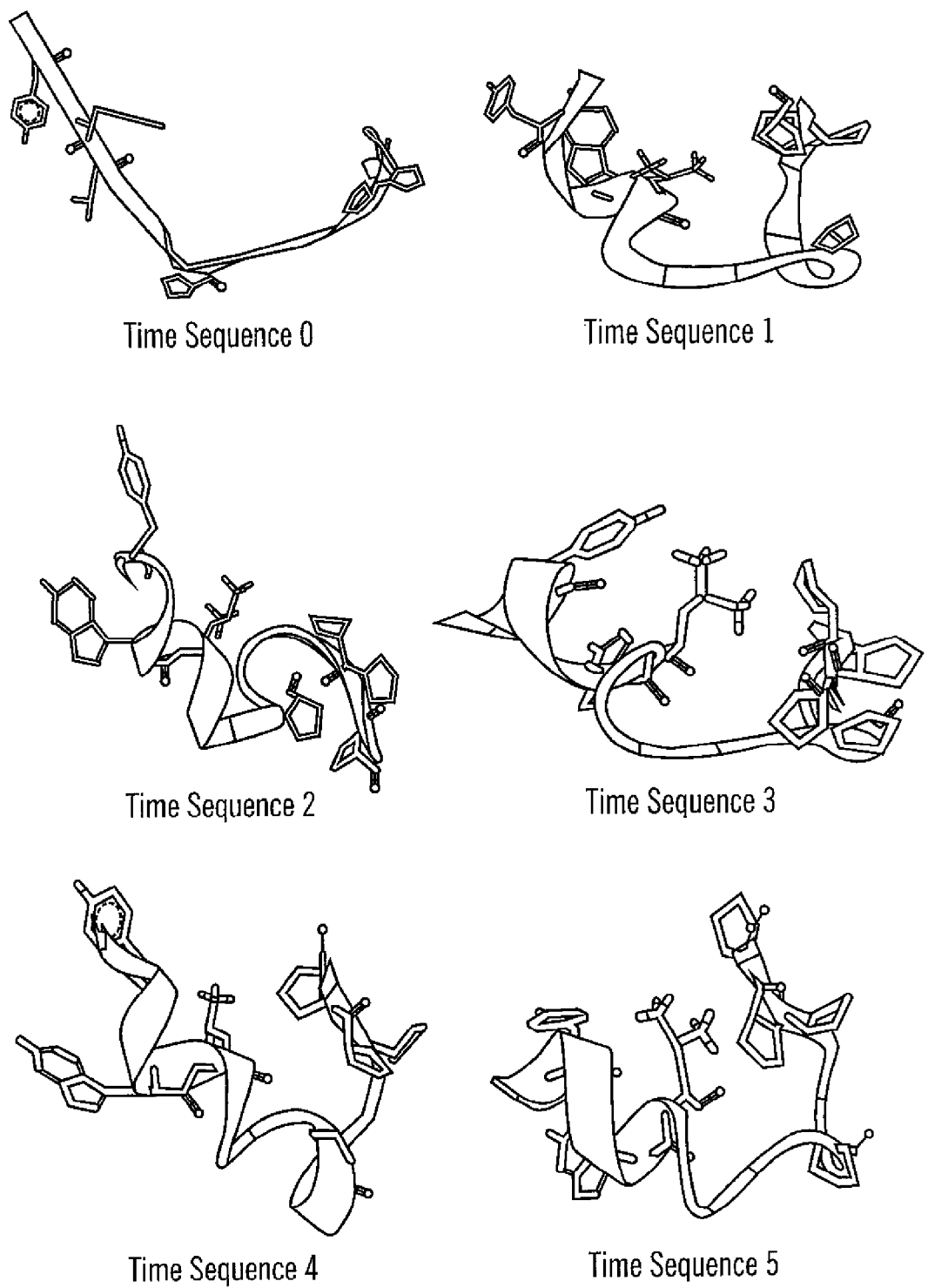
FIG. 17 is a schematic diagram illustrating representative structures for the Trp-cage protein for a particular set of time sequences.

The representative structures for the first 5 time sequences as well as the initial extended structure are shown in FIG. 17. The key hydrophobic residues forming the Trp-cage core, Tyr3, Trp6, Leu7, Pro12, Pro17, Pro18, and Pro19 are represented by sticks, while the rest of the protein are represented by the ribbon view. The first major time sequence (event) shows that α-helix between residues 2 to 9 starts to develop after 0.50 ns (Sequence 1). Interestingly, the $3_{10}$-helix near residues 11 to 14 is also partially formed in the early stage, but it comes and goes from time to time. The α-helix keeps developing, as shown in time sequences 2 (t=~0.76 ns) and time sequence 3 (t=~1.2 ns). During this process, the C-terminal poly-proline II helix has not packed against the α-helix or central trptophan residue yet. The $3_{10}$-helix is reformed at ~1.5 ns (sequence 4).

Meanwhile, another important folding event occurs—the C-terminal poly-proline II helix forms and packs against the α-helix. At approximately 2.0 ns (sequence 5), the sidechain of Trp6 has optimized its position inside the hydrophobic cage formed by the α-helix and poly-proline II helix. Thus, the Trp-cage protein has been folded, with a $C_\alpha$-RMSD of only 2.4 Å from the native structure. These results indicate that the folding process starts with the formation of the α-helix near residues 2-9; then the poly-proline II helix (residues 15-20) forms and packs against the α-helix; and finally the sidechain of Trp6 optimizes its position within the cage formed by the α-helix and the poly-proline II helix. The $3_{10}$ near residues 11-14, on the other hand, comes and goes during the folding process. Once the protein is folded, it can stay in the folded state for quite some time before it unfolds again due to its climbing to high temperatures in the REMD simulation. It should be pointed out that the folding time ~2.0 ns here is much faster than the experimental value of ~4 µs.

This seemingly much faster folding speed is due to at least two important factors: one is that in replica exchange methods the energy barrier crossings can be tens or hundreds times faster than the regular MD and the other is that the folding kinetics in the continuum solvent model GB/SA can be much faster than the experiment as found by others as well. Nevertheless, we are more interested in the time sequential orders of the folding events here. The current method is equally applicable to real time kinetic MD trajectories, once these large scale simulations at biological temperature become accessible.

Figure 18:
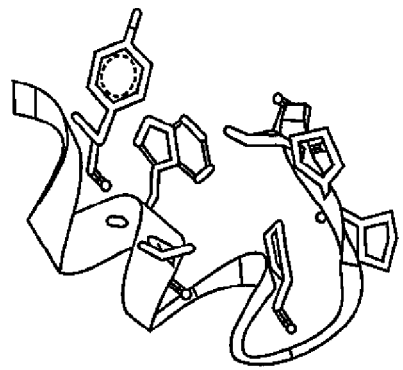
FIG. 18 is a schematic diagram illustrating a lowest all-heavy-atom RMSD structure found with the present invention.
Figure 19:
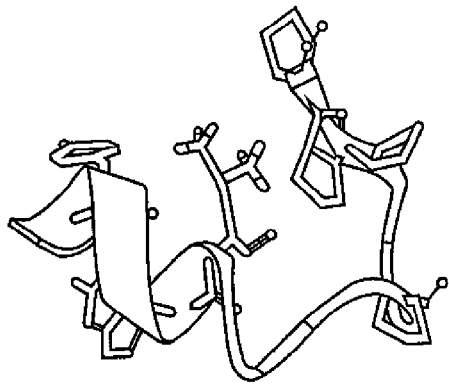
FIG. 19 is a schematic diagram illustrating the representative structure from the folded stated.

Another interesting finding is that all the structures shown in FIG. 17 has a non-perfect Trp6 packing even in the final "folded structure". The Trp6 residue, as the protein name Trp-cage suggests, should be buried inside a hydrophobic cage formed by hydrophobic residues Tyr3, Leu7, Pro12, Pro17, Pro18, and Pro19. However, the current structures show that Trp6 residue is largely pointing away from the central region by exposing its hydrophobic sidechain to the continuum solvent. Since these structures are based on the $C_\alpha$-RMSD data to be consistent with the teachings of U.S. patent application Publication No. 2006/0069515 which has no sidechain information in the calculations, the all-heavy-atom RMSD have been recalculated and the best structures in the trajectory examined. FIG. 18 displays the lowest all-heavy-atom RMSD structure (3.1 Å). It shows a much improved hydrophobic packing for the central Trp6 residue as compared to the above folded structure from the pattern discovery (shown in FIG. 19).

Figure 20:
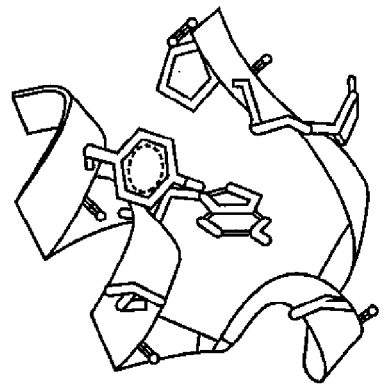
FIG. 20 is a schematic diagram illustrating a native structure.

However, as compared to the native structure (shown in FIG. 20), it still shows a non-perfect packing (less compact) for the hydrophobic residues, particularly, the tendency for Trp6 to point away slightly from the center of the protein. This tendency in Trp6 residue sidechain orientation was not reported in the teachings of U.S. patent application Publication No. 2006/0069515 indicating the power of the combinatorial pattern discovery which can recognize many overlooked structural patterns or motifs. This Trp6 sidechain tendency might be related to the artifacts of the force field AMBER94 used here. It was previously reported that the AMBER94 force field might overestimate the α helix content due to its overly strong backbone torsion parameters, for example, it has been found that there is significant α-helix content for a β-hairpin in explicit solvent using AMBER94 and that the same β-hairpin can be turned into α-helix in continuum solvent GB/SA using the same AMBER94 force field.

The overly strong backbone torsion parameters for the α-helix might have turned the sidechain of Trp6 away from the center of the protein. Nevertheless, large scale simulations with these modern force fields still provide much insight into the protein folding mechanism, and the current pattern discovery algorithm and accompanying visualization tools appear encouraging in revealing important folding events from these folding trajectories.

Exemplary Information Processing System

Figure 21:
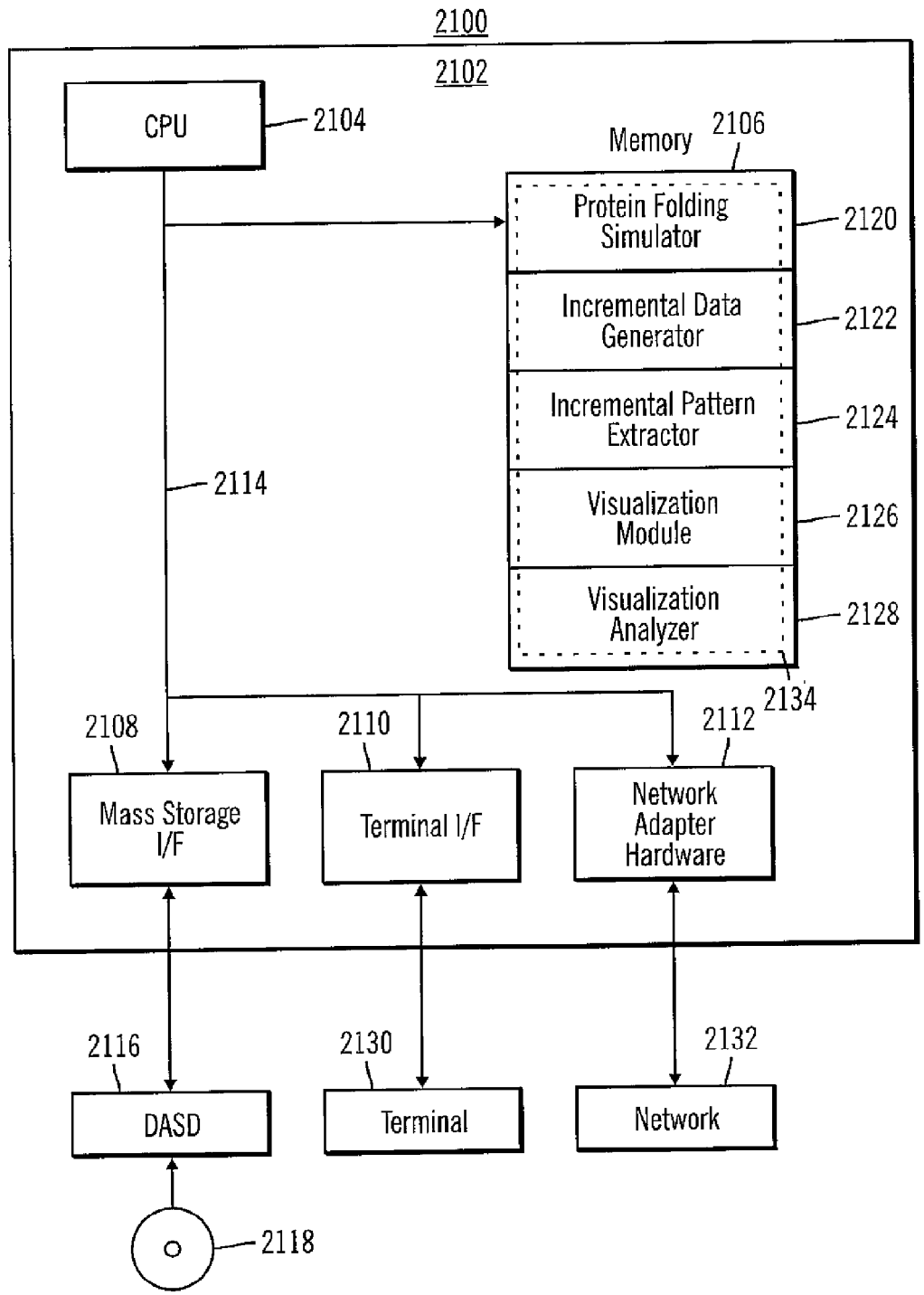
FIG. 21 is an exemplary information processing system according to an embodiment of the present invention.

FIG. 21 is a block diagram illustrating a more detailed view of an information processing system 2100 adapted for performing the process 800 discussed above. The information processing system 2100 is based upon a suitably configured processing system adapted to implement the exemplary embodiment of the present invention. Any suitably configured processing system is similarly able to be used as the information processing system 2100 by embodiments of the present invention, for example, a personal computer, workstation, or the like. The information processing system 2100 includes a computer 2102. The computer 2102 has a processor 2104 that is connected to a main memory 2106, a mass storage interface 2108, terminal interface 2110, and network adapter hardware 2112. Theses system components are connected via a system bus 2114. The mass storage interface 2108 is used to connect mass storage devices, such as data storage device 2116, to the information processing system 2100. One specific type of data storage device is a computer readable medium such as a CD drive or DVD drive, which may be used to store data to and read data from a CD 2118 or DVD, or floppy diskette (not shown). Another type of data storage device is a data storage device configured to support, for example, NTFS type file system operations.

The main memory 2106 comprises an incremental pattern discover module 2134. The incremental pattern discovery module 2134 includes a protein folding simulator 2120 for simulating the folding process of a protein. In one embodiment, the folding protein simulator resides on a remote information processing system in which the results of a simulation are transmitted to the information processing system 2100. The incremental pattern discovery module 2134 also comprises an incremental data generator 2122 for generating incremental patterns, an incremental pattern extractor for extracting pattern sets, a visualization module 2126 for visually displaying patterns and changing landscapes, and a visualization analyzer 2128 for visually analyzing patterns, landscapes, and the like. These components perform the processes discussed above which allow the visual analysis approach for extracting crucial information about protein folding intermediates. Structural motifs that previously overlooked by the free energy landscape analysis can be identified. Force field artifacts can also be identified using the visualization approach performed by these components. In addition, time-correlated folding events or time-sequences of folding intermediates (e.g. which secondary structure forms earlier than the other, or vice versa) can be easily recorded with the visualization process on the fly.

Although illustrated as concurrently resident in the main memory 2106, it is clear that respective components of the main memory 2106 are not required to be completely resident in the main memory 2106 at all times or even at the same time. In one embodiment, the information processing system 2100 utilizes conventional virtual addressing mechanisms to allow programs to behave as if they have access to a large, single storage entity, referred to herein as a computer system memory, instead of access to multiple, smaller storage entities such as the main memory 2106 and data storage device 2116. Note that the term "computer system memory" is used herein to generically refer to the entire virtual memory of the information processing system 2100.

Although only one CPU 2104 is illustrated for computer 2102, computer systems with multiple CPUs can be used equally effectively. Embodiments of the present invention further incorporate interfaces that each includes separate, fully programmed microprocessors that are used to off-load processing from the CPU 2104. Terminal interface 2110 is used to directly connect one or more terminals 2130 to computer 2102 to provide a user interface to the computer 2102. These terminals 2130, which are able to be non-intelligent or fully programmable workstations, are used to allow system administrators and users to communicate with the information processing system 102. The terminal 2130 is also able to consist of user interface and peripheral devices that are connected to computer 2102 and controlled by terminal interface hardware included in the terminal me/F 206 that includes video adapters and interfaces for keyboards, pointing devices, and the like.

An operating system (not shown) included in the main memory is a suitable multitasking operating system such as the Linux, UNIX, Windows XP, and Windows Server 2001 operating system. Embodiments of the present invention are able to use any other suitable operating system. Some embodiments of the present invention utilize architectures, such as an object oriented framework mechanism, that allows instructions of the components of operating system (not shown) to be executed on any processor located within the information processing system 2100. The network adapter hardware 2112 is used to provide an interface to a network 2132. Embodiments of the present invention are able to be adapted to work with any data communications connections including present day analog and/or digital techniques or via a future networking mechanism.

Although the exemplary embodiments of the present invention are described in the context of a fully functional computer system, those of ordinary skill in the art will appreciate that embodiments are capable of being distributed as a program product via floppy disk, e.g. CD 2118 and its equivalents, floppy disk (not shown), or other form of recordable media, or via any type of electronic transmission mechanism.

Non-Limiting Examples

The present invention can be realized in hardware, software, or a combination of hardware and software. A system according to a preferred embodiment of the present invention can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general purpose computer system with a computer program that, when being loaded and executed, controls the computer system such that it carries out the methods described herein.

In general, the routines executed to implement the embodiments of the present invention, whether implemented as part of an operating system or a specific application, component, program, module, object or sequence of instructions may be referred to herein as a "program." The computer program typically is comprised of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A computer implemented method of analyzing a protein folding process, the method comprising:
executing on a processor residing at an information processing system the following:
conducting a trie-based incremental pattern discovery process,
wherein the incremental pattern discovery process comprises:
judging multidimensional data from a simulation of a protein folding process, wherein the simulation produces a continuous stream of raw data for pattern discovery that comprises a set of structural information associated with protein intermediates during the protein folding process;
hierarchically extracting a plurality of distinct and complete incremental patterns as needed from the continuous stream of raw data; and
capturing a set of intermediate data points in the plurality of incremental patterns;
generating a set of pattern landscapes associated with the protein folding process based on the set of intermediate data points that has been captured, the set of pattern landscapes being different and distinct from free energy contour maps, wherein each pattern landscape in the set of pattern landscapes is a hierarchical pattern space with a user defined resolution, wherein the hierarchical pattern space comprises a plurality of levels each comprising a plurality of incremental patterns from the set of incremental patterns where no two distinct patterns are equal at each level;
storing the set of pattern landscapes that has been generated in a memory;
visually displaying one or more pattern landscapes in the set of pattern landscapes to a user;
updating the one or more pattern landscapes that are displayed over a given period time; and
displaying a set of changes associated with the one or more pattern landscapes for the given period of time.

2. The computer implemented method of claim 1, wherein the incremental pattern discovery process further comprises:
extracting an intermediate folding state, which occurs during the protein folding process, from the multidimensional data.

3. The computer implemented method of claim 1, wherein the incremental pattern discovery process further comprises:
simulating the protein folding process to generate a collection of data points;
analyzing the collection of data points;
extracting, based on the analyzing, patterned clusters of data points based on a given set of parameters; and
visually representing the pattern clusters of data points on a display as a pattern landscape.

4. The computer implemented method of claim 3, further comprising:
   filtering the patterned clusters to obtain a set of representative patterns; and
   analyzing the set of representative patterns.

5. The computer implemented method of claim 4, wherein the analyzing comprises:
   extracting at least one configuration of the protein during the protein folding process using a time coordinate; and
   studying a correlation of the parameters and each of the at least one configuration.

6. The computer implemented method of claim 3, wherein the patterned clusters are analyzed and extracted using an incremental pattern discovery algorithm.

7. An information processing system for analyzing a protein folding process, the information processing system comprising:
   a memory;
   a processor communicatively coupled to the memory; and
   an incremental pattern discovery module communicatively coupled to the memory and processor for conducting a trie-based incremental pattern discovery process,
   wherein the incremental pattern discovery process comprises analyzing multidimensional data from a simulation of a protein folding process, wherein the simulation produces a continuous stream of raw data for pattern discovery that comprises a set of structural information associated with protein intermediates during the protein folding process; and
   wherein the incremental pattern discovery module is further for:
      hierarchically extracting a plurality of distinct and complete incremental patterns as needed from the continuous stream of raw data; and
      capturing a set of intermediate data points in the plurality of incremental patterns;
      generating a set of pattern landscapes associated with the protein folding process based on the set of intermediate data points that has been captured, the set of pattern landscapes being different and distinct from free energy contour maps, wherein each pattern landscape in the set of pattern landscapes is a hierarchical pattern space with a user defined resolution, wherein the hierarchical pattern space comprises a plurality of levels each comprising a plurality of incremental patterns from the set of incremental patterns where no two distinct patterns are equal at each level;
      visually displaying one or more pattern landscapes in the set of pattern landscapes to a user;
      updating the one or more pattern landscapes that are displayed over a given period time; and
      displaying a set of changes associated with the one or more pattern landscapes for the given period of time.

8. The information processing system of claim 7, wherein the incremental pattern discovery module is further for at least one of:
   extracting an intermediate folding state, which occurs during the protein folding process, from the multidimensional data;
   simulating the protein folding process to generate a collection of data points;
   analyzing the collection of data points;
   extracting, based on the analyzing, patterned clusters of data points based on a given set of parameters;
   visually representing the pattern clusters of data points on a display as a pattern landscape; and
   filtering the patterned clusters to obtain a set of representative patterns; and
   analyzing the set of representative patterns.

9. The information processing system of claim 8, wherein the analyzing by incremental pattern discovery module further comprises:
   extracting at least one configuration of the protein during the protein folding process using a time coordinate; and
   studying a correlation of the parameters and each of the at least one configuration.

10. The information processing system of claim 8, wherein the patterned clusters are analyzed and extracted using an incremental pattern discovery algorithm.

11. A physically embodied computer readable medium for analyzing a protein folding process, the computer readable medium comprising instructions for:
    conducting a trie-based incremental pattern discovery process,
    wherein the incremental pattern discovery process comprises:
       analyzing multidimensional data from a simulation of a protein folding process, wherein the simulation produces a continuous stream of raw data for pattern discovery that comprises a set of structural information associated with protein intermediates during the protein folding process;
       hierarchically extracting a plurality of distinct and complete incremental patterns as needed from the continuous stream of raw data; and
       capturing a set of intermediate data points in the plurality of incremental patterns;
    generating a set of pattern landscapes associated with the protein folding process based on the set of intermediate data points that has been captured, the set of pattern landscapes being different and distinct from free energy contour maps, wherein each pattern landscape in the set of pattern landscapes is a hierarchical pattern space with a user defined resolution, wherein the hierarchical pattern space comprises a plurality of levels each comprising a plurality of incremental patterns from the set of incremental patterns where no two distinct patterns are equal at each level;
    storing the set of pattern landscapes that has been generated in a memory;
    visually displaying one or more pattern landscapes in the set of pattern landscapes to a user;
    updating the one or more pattern landscapes that are displayed over a given period time; and
    displaying a set of changes associated with the one or more pattern landscapes for the given period of time.

12. The physically embodied computer readable medium of claim 11, wherein the instructions for the incremental pattern discovery process further comprise instructions for at least one of:
    extracting an intermediate folding state, which occurs during the protein folding process, from the multidimensional data;
    simulating the protein folding process to generate a collection of data points;
    analyzing the collection of data points;
    extracting, based on the analyzing, patterned clusters of data points based on a given set of parameters, wherein the patterned clusters are analyzed and extracted using an incremental pattern discovery algorithm;
    visually representing the pattern clusters of data points on a display as a pattern landscape;

filtering the patterned clusters to obtain a set of representative patterns; and
analyzing the set of representative patterns.

13. The physically embodied computer readable medium of claim 12, wherein the instructions for the analyzing further comprise instructions for:
extracting at least one configuration of the protein during the protein folding process using a time coordinate; and
studying a correlation of the parameters and each of the at least one configuration.

* * * * *